United States Patent
Corselli

(10) Patent No.: US 9,632,096 B2
(45) Date of Patent: Apr. 25, 2017

(54) METHODS OF ASSESSING THE IMMUNOMODULATORY POTENTIAL OF A MULTIPOTENT STROMAL CELL (MSC) POPULATION, AND SYSTEMS AND KITS FOR PRACTICING THE SAME

(71) Applicant: Becton, Dickinson and Company, Franklin Lakes, NJ (US)

(72) Inventor: Mirko Corselli, San Diego, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 102 days.

(21) Appl. No.: 14/530,584

(22) Filed: Oct. 31, 2014

(65) Prior Publication Data

US 2015/0125881 A1     May 7, 2015

Related U.S. Application Data

(60) Provisional application No. 61/899,835, filed on Nov. 4, 2013.

(51) Int. Cl.
| | |
|---|---|
| *G01N 15/14* | (2006.01) |
| *G01N 33/68* | (2006.01) |
| *G01N 33/50* | (2006.01) |
| *G01N 33/569* | (2006.01) |
| *G01N 15/10* | (2006.01) |

(52) U.S. Cl.
CPC ......... *G01N 33/6872* (2013.01); *G01N 15/14* (2013.01); *G01N 15/1459* (2013.01); *G01N 33/5091* (2013.01); *G01N 33/56966* (2013.01); *G01N 33/6869* (2013.01); *G01N 2015/1006* (2013.01); *G01N 2015/1402* (2013.01);

(Continued)

(58) Field of Classification Search
CPC .............. G01N 15/14; G01N 15/1459; G01N 33/5091; G01N 33/6869; G01N 33/6872; G01N 33/56966; G01N 2333/5412; G01N 2333/70525; G01N 2015/1006; G01N 2015/148; G01N 2015/1402
See application file for complete search history.

(56) References Cited

U.S. PATENT DOCUMENTS

| | | |
|---|---|---|
| 2010/0172885 A1 | 7/2010 | Pittenger et al. |
| 2011/0045071 A1 | 2/2011 | Hematti et al. |

(Continued)

FOREIGN PATENT DOCUMENTS

WO      2014113704 A2     7/2014

OTHER PUBLICATIONS

Gebler et al. The immunomodulatory capacity of mesenchymal stem cells, Trends in Molecular Medicine 18 (2): 128-134 (Feb. 2012).*

(Continued)

*Primary Examiner* — Gail R Gabel
(74) *Attorney, Agent, or Firm* — Bret E. Field; Bozicevic, Field & Francis LLP

(57) ABSTRACT

Methods of assessing the immunomodulatory potential of a multipotent stromal cell (MSC) population are provided. Aspects of the methods include evaluating the amount of CD54/IL-6 associated with an MSC in a sample of the MSC population to obtain a CD54/IL-6 result and providing an assessment of the immunomodulatory potential of the MSC population based on the obtained CD54/IL-6 result. Also provided are systems and kits that find use in practicing the subject methods.

18 Claims, 4 Drawing Sheets

(52) U.S. Cl.
CPC .......... *G01N 2015/149* (2013.01); *G01N 2333/5412* (2013.01); *G01N 2333/70525* (2013.01)

(56) References Cited

U.S. PATENT DOCUMENTS

| | | | |
|---|---|---|---|
| 2015/0004146 A1* | 1/2015 | Peled | A61K 35/28 424/93.7 |
| 2016/0130556 A1* | 5/2016 | Hantash | C12N 5/0667 424/93.7 |

OTHER PUBLICATIONS

Francois et al., "Human MSC suppression correlates with cytokine induction of indoleamine 2,3-dioxygenase and bystander M2 macrophage differentiation.", Mol Ther. (Jan. 2012), 20(1);187-95.

Le Blanc et al. "Multipotent mesenchymal stromal cells and the innate immune system.", Nat Rev Immunol. (Apr. 2012), 12(5):383-96.

Melief et al., "Adipose tissue-derived multipotent stromal cells have a higher immunomodulatory capacity than their bone marrow-derived counterparts.", Stem Cells Transl Med. (Jun. 2013), 2(6):455-63.

Menard et al, "Clinical-grade mesenchymal stromal cells produced under various good manufacturing practice processes differ in their immunomodulatory properties: standardization of immune quality controls.", Stem Cells Dev. (Jun. 2013), 22(12):1789-801.

Gebler et al. "The immunomodulatory capacity of mesenchymal stem cells", Trends in Molecular Medicine, Feb. 2012, vol. 18, No. 2, pp. 128-134.

* cited by examiner

METHODS OF ASSESSING THE IMMUNOMODULATORY POTENTIAL OF A MULTIPOTENT STROMAL CELL (MSC) POPULATION, AND SYSTEMS AND KITS FOR PRACTICING THE SAME

CROSS-REFERENCE TO RELATED APPLICATIONS

Pursuant to 35 U.S.C. §119 (e), this application claims priority to the filing date of the U.S. Provisional Patent Application Ser. No. 61/899,835, filed Nov. 4, 2013, the disclosure of which is incorporated herein by reference.

INTRODUCTION

Multipotent stromal cells (MSCs), also referred to in the field as mesenchymal stem cells, have a number of therapeutic uses due to their regenerative properties and immunomodulatory potential. The International Society for Cellular Therapy classifies MSCs through their adhesion to plastic, their expression of CD73, CD90 and CD105, and their potential to give rise to multiple mesenchymal lineages, specifically to osteoblasts, adipocytes and chondroblasts. However, no definition of MSCs is definitive, as differences in MSC populations result from tissue of origin and culture conditions. MSCs are typically immunosuppressive, and have been shown to inhibit T-cell and B-cell proliferation, promote the differentiation of certain subsets of T-cells into regulatory T-cells, and inhibit monocyte differentiation into dendritic cells. Upon activation of MSCs, such as through exposure to IFN-γ and/or TNF-α, this immunomodulatory potential is typically increased. Both soluble factors and direct cell-cell contact are mechanisms of MSC immunomodulatory activity.

Such immunomodulatory potential makes MSCs a candidate cellular therapy for of autoimmune and/or inflammatory diseases, including but not limited to graft-versus host disease, Chron's disease, and multiple sclerosis. Additional factors make MSCs even stronger candidates for cell therapies, including: their ease of isolation and expansion to clinical scales; conservation of potency after cryo-preservation; and a lack of elicited adverse reactions upon allogeneic MSC transplantation.

MSCs are typically harvested from bone marrow or adipose tissue. Due to the relative rarity of MSCs and stem cells that give rise to MSCs (often a fraction of a percent), MSCs are typically expanded in vitro prior to therapeutic use. Factors such as the tissue of origin and culture conditions under which MSCs are expanded are understood to affect the immunomodulatory potential and potency of the resulting MSC population, which may in turn impact the quality of MSC populations used in cell-based therapies.

SUMMARY

Methods of assessing the immunomodulatory potential of a multipotent stromal cell (MSC) population are provided. Aspects of the methods include evaluating the amount of CD54/IL-6 associated with an MSC in a sample of the MSC population to obtain a CD54/IL-6 result and providing an assessment of the immunomodulatory potential of the MSC population based on the obtained CD54/IL-6 result. Also provided are systems and kits that find use in practicing the subject methods.

BRIEF DESCRIPTION OF THE FIGURES

FIG. 2 panel A provides the gating strategy used to obtain the peripheral blood mononuclear cells (PBMCs), specifically CD3+ T-cells, assayed in FIG. 2 panels B and C. FIG. 2 panel B shows IFN-γ expression in resting PBMCs, in stimulated PBMCs. Stimulated PBMCs were cultured alone or in co-culture with MSCs derived from either bone marrow (BM MSCs) or adipose tissue (AT MSCs). FIG. 2 panel C shows a violet proliferation dye (VPD) stain of PBMCs under the conditions described for FIG. 2 panel B.

FIG. 3 panel A shows a gating strategy useful for obtaining MSCs. FIG. 3 panel B shows expression of CD54, CD274, and IL-6 in BM MSCs and AT MSCs before (red boxes) and after co-culture with stimulated PBMCs.

FIG. 4 panel A shows CD54 and IL-6 to be more highly expressed in AT MSCs as compared to BM MSCs. FIG. 4 panel B shows reduced IFN-γ expression in T-cells co-cultured with AT MSCs as oppose to T-cells co-cultured with BM MSCs. FIG. 4 panel C shows reduced proliferation of T-cells co-cultured with AT MSCs as compared to BM MSCs.

DETAILED DESCRIPTION

Figure 1:
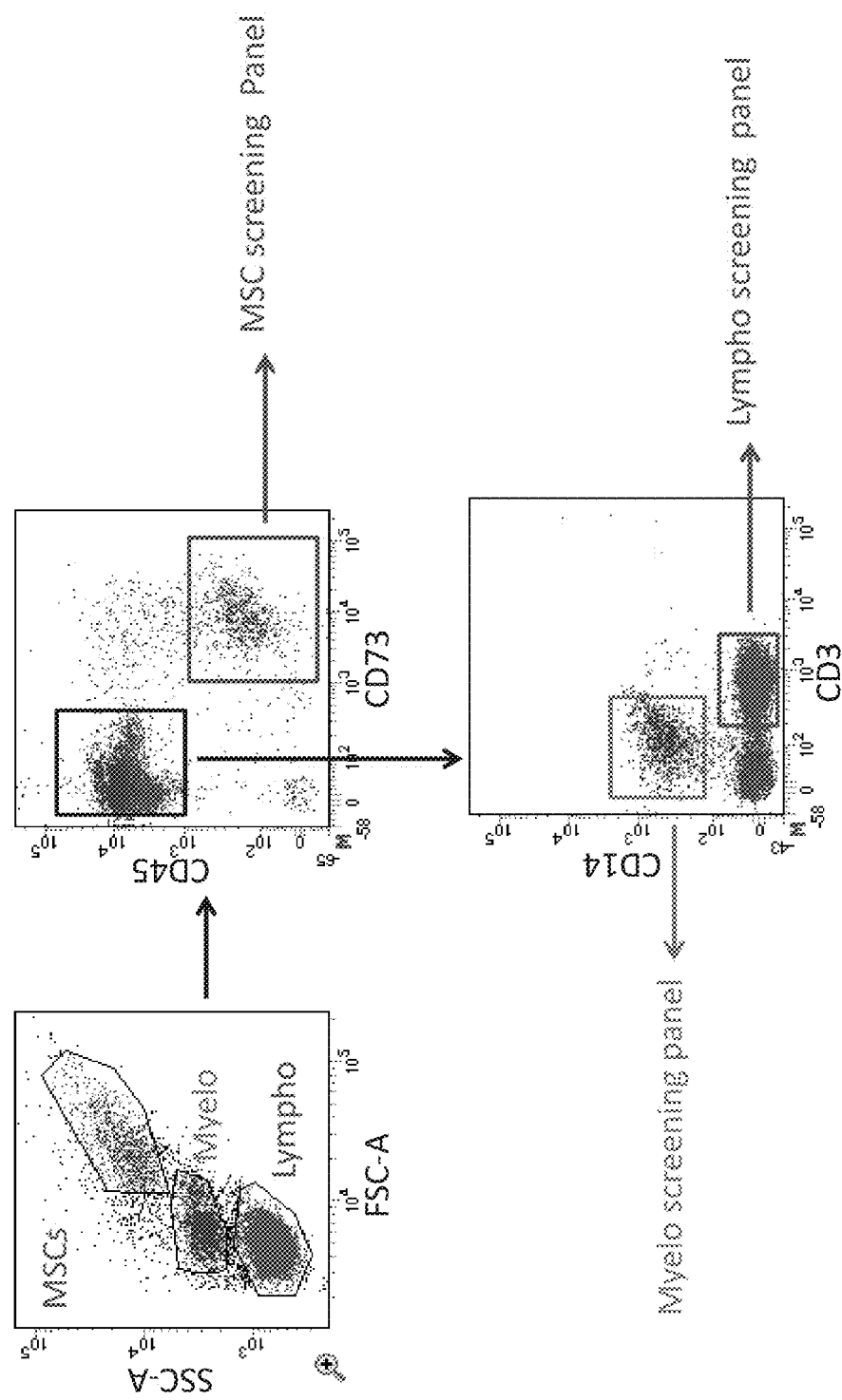
FIG. 1 provides a gating strategy for separating multipotent stromal cell (MSC), myelocyte and lymphocyte populations by flow cytometry. Cell populations are separated based on a combination of forward scatter (FSC) and side scatter (SSC) as well as CD45, CD73, CD14 and CD3 expression. Each population can be further screened for surface markers and/or cytokines under different conditions (e.g., alone or in co-culture, before and after stimulation). In this particular gating strategy, the lymphocyte subset (in red) consists primarily of T-cells, due to gating on CD3.

Methods of assessing the immunomodulatory potential of a multipotent stromal cell (MSC) population are provided. Aspects of the methods include evaluating the amount of CD54/IL-6 associated with an MSC in a sample of the MSC population to obtain a CD54/IL-6 result and providing an assessment of the immunomodulatory potential of the MSC population based on the obtained CD54/IL-6 result. Also provided are systems and kits that find use in practicing the subject methods.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Methods recited herein may be carried out in any order of the recited events which is logically possible, as well as the recited order of events.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

In further describing embodiments of the invention, aspects of embodiments of the methods will be described first in greater detail. Next, embodiments of systems and kits that may be used in practicing methods of the invention are reviewed.

Methods

As summarized above, embodiments of the invention are directed to methods of assessing the immunomodulatory potential of a multipotent stromal cell (MSC) population. MSCs may be plastic adherent and are capable of differentiation into multiple mesenchymal lineages, such as osteoblasts, adipocytes, myoblasts and chondroblasts. Human MSCs may be positive for surface markers CD73, CD90, and CD105, and negative for surface markers CD34, CD45, CD14, CD11b, and CD19. In addition, other markers such as CD271, COX2, IDO, CD274, CD44, CD166, STRO-1 may be useful in identifying and/or characterizing human MSCs or subsets thereof. A thorough review of MSC populations and MSC surface markers can be found Hass R. et al., Cell Commun Signal. (2011) 14; 9:12.

In certain aspects, the MSC population may be produced by first obtaining cells (including MSCs and/or stem cells (SCs)) from mammalian tissue. The mammalian tissue may be obtained from a human, non-human primate, murine, or another suitable mammal. The tissue may be bone marrow, adipose tissue, peripheral blood, or another tissue suitable for producing MSCs.

For isolation of cells from tissue, an appropriate dispersion or suspension liquid may be used, as desired. The solution may be a balanced salt solution, e.g., normal saline, PBS, Hank's balanced salt solution, etc., conveniently supplemented with fetal calf serum, human platelet lysate or other factors, in conjunction with an acceptable buffer at low concentration, such as from 5-25 mM. Convenient buffers include HEPES, phosphate buffers, lactate buffers, etc. The separated cells may be collected in any appropriate medium that maintains the viability of the cells. Various media are commercially available and may be used according to the nature of the cells, including dMEM, HBSS, dPBS, RPMI, Iscove's medium, etc., frequently supplemented with fetal calf serum or human platelet lysate.

The obtained cells may then be cultured under conditions suitable for MSC production and/or expansion. The culture conditions may include one or more passages and in some instances ten or fewer passages. The culture conditions may include one or more factors for maintaining multipotency in cells. Examples of such factors include fetal bovine serum (FBS), human platelet lysate, vectors for transfecting genes for inducing/maintaining pluripotency, etc. The MSC population may be frozen (e.g., in 5% or greater DMSO and at liquid nitrogen temperatures) prior to use, as desired.

MSC as described above can be propagated continuously in culture, using culture conditions that promote proliferation without promoting differentiation, as desired. The cells can be maintained in medium, e.g., DMEM, RPMI, etc., in the presence of fetal bovine serum or serum-free replacement without differentiation. The cells may be passaged at 75 to 95% confluence, using a protease, e.g., trypsin, collagenase, etc. Due to the multipotency of MSCs, and despite their relative rarity in their tissue of origin (often a fraction of a percent), MSCs propagated in culture may be enriched to levels suitable for clinical applications.

In certain aspects, a substantially pure population of MSCs may be obtained by enriching for MSCs or SCs that are precursors to MSCs, wherein any convenient protocol for doing so may be employed. For example, beads conjugated to antibodies (or another binding molecule) that specifically bind to non-MSC surface markers may be used to deplete non-MSC cells. Beads conjugated to antibodies specific for MSC surface markers may be used to separate MSCs from other cells in. In another example, a gating strategy similar to that illustrated in FIG. 1 may be employed on a fluorescence activated cell sorter (FACS) instrument to purify the MSC population.

Figure 2:
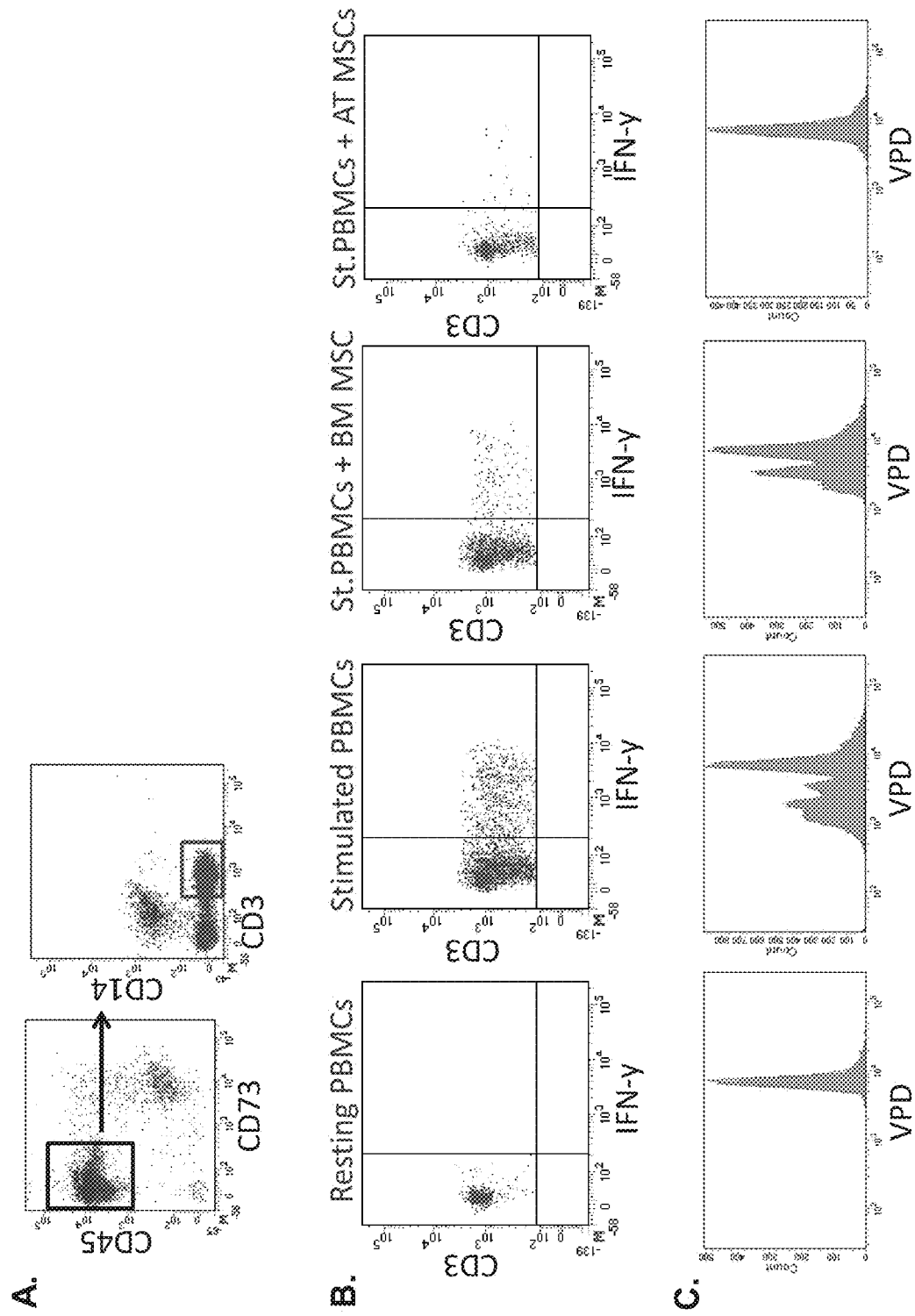
FIG. 2 panels A to C provide results of a flow cytometric assay showing the immunomodulatory activity of MSCs on T-cell expression of IFN-γ and T-cell proliferation.

The immunomodulatory potential of the MSC population may be an ability of the MSC population to suppress proliferation and/or activation of certain immune cells, such as T-cells, B-cells, NK-cells, or combinations thereof. Immunomodulatory potential of the MSC population may also include the ability of the MSCs in the population to modulate immune cell development (e.g., induce T-cell differentiation into regulatory T-cells, prevent monocyte differentiation into dendritic cell, etc.). For example, as illustrated in FIG. 2, co-culture of bone marrow derived MSCs (BM MSCs) or adipose tissue derived MSCs (AT MSCs) with stimulated PBMCs attenuated both T-cell IFN-γ expression and proliferation.

In some instances of the subject methods, a sample (e.g., an aliquot) is obtained from the MSC population and assayed to obtain an assessment of the immunomodulatory potential of the MSC population from which the sample was obtained. The sample of the MSC population (used herein interchangeably with "aliquot" and "sample") may be cultured (e.g., under similar conditions as described for the MSC population above) and/or frozen prior to use in aspects of the methods disclosed herein.

Aspects of the invention include contacting a sample of the MSC population of interest with one or more detectable labels to obtain a labeled sample. A detectable label may include a specific binding domain and a label domain. The terms "specific binding," "specifically binds," and the like, refer to the preferential binding of a domain (e.g., one binding pair member to the other binding pair member of the same binding pair) relative to other molecules or moieties in a solution or reaction mixture. The specific binding domain may bind (e.g., covalently or non-covalently) to a specific epitope within the cell. In certain aspects, specific binding domain non-covalently binds to a target. In such instances, the specific binding domain association with the binding target (e.g., CD54, IL-6 or another biomarker) may be characterized by a KD (dissociation constant) of $10^{-5}$ M or less, $10^{-6}$ M or less, such as $10^{-7}$ M or less, including $10^{-8}$ M or less, e.g., $10^{-9}$ M or less, $10^{-10}$ M or less, $10^{-11}$ M or less, $10^{-12}$ M or less, $10^{-13}$ M or less, $10^{-14}$ M or less, $10^{-15}$ M or less, including $10^{-16}$ M or less. A variety of different types of specific binding domains may be employed as the capture ligands. Specific binding domains of interest include, but are not limited to, antibody binding agents, proteins, peptides, haptens, nucleic acids, etc. The term "antibody binding agent" as used herein includes polyclonal or monoclonal antibodies or fragments that are sufficient to bind to an analyte of interest. The antibody fragments can be, for example, monomeric Fab fragments, monomeric Fab' fragments, or dimeric F(ab)'2 fragments. Also within the scope of the term "antibody binding agent" are molecules produced by antibody engineering, such as single-chain antibody molecules (scFv) or humanized or chimeric antibodies produced from monoclonal antibodies by replacement of the constant regions of the heavy and light chains to produce chimeric antibodies or replacement of both the constant regions and the framework portions of the variable regions to produce humanized antibodies.

The label domain may be detectable based on, for example, fluorescence emission maxima, fluorescence polarization, fluorescence lifetime, light scatter, mass, molecular mass, or combinations thereof. In certain aspects, the label domain may be a fluorophore (i.e., a fluorescent label, fluorescent dye, etc.). Fluorophores can be selected from any of the many dyes suitable for use in analytical applications (e.g., flow cytometry, imaging, etc.). A large number of dyes are commercially available from a variety of sources, such as, for example, Molecular Probes (Eugene, Oreg.) and Exciton (Dayton, Ohio). Examples of fluorophores that may be incorporated into the microparticles include, but are not limited to, 4-acetamido-4'-isothiocyanatostilbene-2,2'disulfonic acid; acridine and derivatives such as acridine, acridine orange, acridine yellow, acridine red, and acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate (Lucifer Yellow VS); N-(4-anilino-1-naphthyl)maleimide; anthranilamide; Brilliant Yellow; coumarin and derivatives such as coumarin, 7-amino-4-methylcoumarin (AMC, Coumarin 120), 7-amino-4-trifluoromethylcoulurarin (Coumaran 151); cyanine and derivatives such as cyanosine, Cy3, Cy5, Cy5.5, and Cy7; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylaminocoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl) aminofluorescein (DTAF), 2'7'-dimethoxy-4'5'-dichloro-6-carboxyfluorescein (JOE), fluorescein isothiocyanate (FITC), fluorescein chlorotriazinyl, naphthofluorescein, and QFITC (XRITC); fluorescamine; IR144; IR1446; Green Fluorescent Protein (GFP); Reef Coral Fluorescent Protein (RCFP); Lissamine™; Lissamine rhodamine, Lucifer yellow; Malachite Green isothiocyanate; 4-methylumbelliferone; ortho cresolphthalein; nitrotyrosine; pararosaniline; Nile Red; Oregon Green; Phenol Red; B-phycoerythrin; o-phthaldialdehyde; pyrene and derivatives such as pyrene, pyrene butyrate and succinimidyl 1-pyrene butyrate; Reactive Red 4 (Cibacron™ Brilliant Red 3B-A); rhodamine and derivatives such as 6-carboxy-X-rhodamine (ROX), 6-carboxyrhodamine (R6G), 4,7-dichlororhodamine lissamine, rhodamine B sulfonyl chloride, rhodamine (Rhod), rhodamine B, rhodamine 123, rhodamine X isothiocyanate, sulforhodamine B, sulforhodamine 101, sulfonyl chloride derivative of sulforhodamine 101 (Texas Red), N,N,N',N'-tetramethyl-6-carboxyrhodamine (TAMRA), tetramethyl rhodamine, and tetramethyl rhodamine isothiocyanate (TRITC); riboflavin; rosolic acid and terbium chelate derivatives; xanthene; or combinations thereof. Other fluorophores or combinations thereof known to those skilled in the art may also be used, for example those available from Molecular Probes (Eugene, Oreg.) and Exciton (Dayton, Ohio). The fluorescent label may be distinguishable based on fluorescence emission maxima, and optionally further based on light scatter or extinction.

In other aspects, the label domain may be a metal isotope detectable by mass spectroscopy, such as by the time of flight mass spectrometer used in mass cytometery, e.g., as described in international patent application serial no. PCT/US2012/020950 published as WO/2010/097070, the disclosure of which is herein incorporated by reference.

In certain aspects, the sample of the MSC population is contacted with (e.g., exposed to, stained with, labeled by) a first detectable label that specifically binds to CD54. CD54, also known as intercellular adhesion molecule 1 (ICAM-1), is understood to bind to integrins (CD11a/CD18 and CD11b/CD18) and thereby stabilize cell-cell interactions. Human CD54 is described in, among other locations, the website having an address produced by placing "http://" in front of "omim.org/entry/147840?search=cd54&highlight=cd54."
The sample of the MSC population may also be contacted with a second detectable label that specifically binds to IL-6. IL-6 activity is context dependent, and it has both pro-inflammatory and anti-inflammatory properties. Human IL-6 is described in, among other locations, the website having an address produced by placing "http://" before "omim.org/entry/147620?search=il6&highlight=il6."

In certain aspects, the method may involve treating the sample of the MSC population with a protein transport inhibitor, e.g., prior to contacting the sample (and cells therein) with the second detectable label in the sample of the MSC population. Examples of protein transport inhibitors include Brefeldin A and Monensin, although other protein transport inhibitors may also be employed, as desired. Pretreating the MSC population with a protein transport inhibitor may allow for the accumulation of normally secreted proteins (such as IL-6 and other cytokines) which would otherwise be difficult to detect. The MSC population may be pretreated with the protein transport inhibitor for an amount of time sufficient to accumulate normally secreted proteins, such as from 5 minutes to 1 day, 30 minutes to 6 hours, or 1 hour to 2 hours.

In certain aspects, the method may include fixing the sample, for example, before contacting the sample with the first and second detectable labels, before contacting the sample with the second detectable label, and/or after contacting the sample with the second detectable label. The cells of the sample may be fixed through exposure to any of a number of cell fixing agents (i.e., fixation reagents), such as paraformaldehyde, glutaraldehyde, methanol, acetone, formalin, or any combination thereof. Other fixatives and fixation methods may be employed, as desired. Fixation time may vary, and in some instances ranges from 1 minute and 1 hour, such as 5 minutes and 30 minutes. The temperature at which fixation takes place may vary, and in some instances the temperature ranges from −30° C. to 30° C.

In certain aspects, the sample may be treated with a permeabilization agent prior to contacting the sample with the second detectable label. Permeabilization may allow the second detectable label to enter cells in the sample and specifically bind to IL-6. Permeabilization may take place before, after, or at the same time as the fixation previously described. The cells of the sample may be permeabilized through exposure to any of a number of cell permeabilizing agents, such as methanol, acetone or a detergent (e.g., triton, NP-40, saponin, tween 20, digitonin, leucoperm, etc.), or a combination thereof. Permeabilization time may vary, and in some instances ranges from 1 minute to 1 hour, such as from 5 minutes to 30 minutes. The temperature at which permeabilization takes place may vary, and in some instances the temperature may range from 0° C. to 50° C.

The sample of the MSC population may optionally be contacted with one or more additional detectable labels. An additional detectable label may specifically bind to an additional biomarker of interest (e.g., a biomarker indicative of MSC immunomodulatory potential). For example, the additional biomarker may be CD271, COX2, IDO, CD274, CD44, CD166, STRO-1, or any other biomarker understood to play a role in MSC cell-cell interactions, proliferation, and/or immunomodulatory potential. Optionally, the additional biomarker may be useful for distinguishing MSCs from other cell types.

The sample may be contacted with the detectable labels (e.g., the first, second, and/or additional detectable labels) at the same time or in succession. The sample may be contacted with a sufficient amount of the detectable labels and for a period of time sufficient to allow binding of detectable labels to their specific targets (e.g., CD54, IL-6, an additional biomarker, etc.). For example, the sample may be contacted for between 5 minutes and several hours, such as between 30 minutes and 2 hours. The sample may be maintained at any convenient temperature, e.g., between freezing and room temperature, during the contacting step. A washing step may then be performed, as desired, e.g., to remove any unbound detectable labels and other sample components. Washing may be performed using any convenient protocol, such as by combining the reaction mixture with a suitable wash buffer (e.g., PBS, HEPES) and separating the cells from the fluid. A given washing protocol may include one or more distinct washing steps, as desired. Following any washing protocol, the cells may be re-suspended in a suitable liquid (e.g., the washing buffer or another buffer).

Following contacting the sample of the MSC population with detectable labels to obtain a labeled sample (e.g., as described above), aspects of the methods include evaluating, e.g., quantitating, the amount of the first and second detectable labels associated with MSC(s) in the sample to obtain a CD54/IL-6 result. The evaluation may be qualitative, e.g., a determination that the amount is above or below a predetermined threshold, or quantitative, e.g., a determination of a value or level representative of the copy number of the target molecule. An amount of a detectable label associated with a cell, e.g., bound to the surface of a cell, present inside of a cell, etc., may be evaluated, e.g., quantified based on the intensity (e.g., fluorescence intensity) of a signal produced by the label domain of the detectable label that is associated with the cell. The CD54/IL-6 result may be the quantitated amount of the first and second detectable labels in a single MSC or as averaged across a number of MSCs. The CD54/IL-6 result may relate to an expression level of CD54 and IL-6. The method may optionally include quantitating the amount of one or more additional detectable labels to obtain an additional result (e.g., quantitated in any of the ways described for the CD54/IL-6 result).

In certain embodiments, quantitating the amount of each of the detectable labels (i.e., the first, second, and/or additional detectable labels) may include distinguishing the detectable labels based on fluorescence emission maxima. For example, fluorescence compensation between two or more detectable labels with spectral overlap may be employed to distinguish the signal (e.g., fluorescence emission) resulting from each of the detectable labels. Two or more detectable labels may also be distinguished based on light scattering, fluorescence lifetime, excitation spectra, or combinations thereof.

In some instances, the detectable labels may be quantified by flow cytometry. Flow cytometry is a methodology using multi-parameter data for identifying and distinguishing between different particles, such as cells or beads, that vary from one another (e.g., in terms of label, size, granularity, etc.) in a fluid medium. In flow cytometrically analyzing the particles (e.g., the cells prepared as described above), a liquid medium comprising the particles is first introduced into the flow path of the flow cytometer. When in the flow path, the particles are passed substantially one at a time through one or more sensing regions, where each of the particles is exposed individually to a source of monochromatic light and measurements of light scatter parameters and/or fluorescent emissions as desired (e.g., two or more light scatter parameters and measurements of one or more fluorescent emissions) are separately recorded for each particle. The data recorded for each particle is analyzed in real time or stored in a data storage and analysis means, such as a computer, as desired. U.S. Pat. No. 4,284,412 describes the configuration and use of a typical flow cytometer equipped with a single light source while U.S. Pat. No. 4,727,020 describes the configuration and use of a flow cytometer equipped with two light sources. The disclosures of these patents are herein incorporated by reference. Flow cytometers having more than two light sources may also be employed.

More specifically, in a flow cytometer, the particles are passed, in suspension, substantially one at a time in a flow path through one or more sensing regions where in each region each particle is illuminated by an energy source. The energy source may include an illuminator that emits light of a single wavelength, such as that provided by a laser (e.g., He/Ne or argon) or a mercury arc lamp with appropriate filters. For example, light at 488 nm may be used as a wavelength of emission in a flow cytometer having a single sensing region. For flow cytometers that emit light at two distinct wavelengths, additional wavelengths of emission light may be employed, where specific wavelengths of interest include, but are not limited to: 535 nm, 635 nm, and the like.

In series with a sensing region, a detector module that includes one or more detectors, e.g., light collectors, such as photomultiplier tubes (or "PMT"), is used to record light that passes through each particle (generally referred to as forward light scatter), light that is reflected orthogonal to the direction of the flow of the particles through the sensing region (generally referred to as orthogonal or side light scatter) and fluorescent light emitted from the particles, if it is labeled with fluorescent marker(s), as the particle passes through the sensing region and is illuminated by the energy source. Each of forward light scatter (or FSC), orthogonal light scatter (SSC), and fluorescence emissions comprise a separate parameter for each particle (i.e. each "event"). Thus, for example, two, three four or more parameters can be collected (and recorded) from a particle labeled with two different fluorescence markers.

Accordingly, in flow cytometrically assaying the particles, the particles which may include different amounts of the first, second, and/or additional detectable labels are detected and uniquely identified by exposing the particles to excitation light and measuring the fluorescence of each particle in one or more detection channels, as desired. The excitation light may be from one or more light sources and may be either narrow or broadband. Examples of excitation light sources include lasers, light emitting diodes, and arc lamps. Fluorescence emitted in detection channels used to identify the particles and binding complexes associated therewith may be measured following excitation with a single light source, or may be measured separately following excitation with distinct light sources. If separate excitation light sources are used to excite the particle labels, the labels may be selected such that all the labels are excitable by each of the excitation light sources used.

Flow cytometers further include data acquisition, analysis and recording means, such as a computer, wherein multiple data channels record data from each detector for the light scatter and fluorescence emitted by each particle as it passes through the sensing region. The purpose of the analysis system is to classify and count particles wherein each particle presents itself as a set of digitized parameter values. In flow cytometrically assaying particles in methods of the invention, the flow cytometer may be set to trigger on a selected parameter in order to distinguish the particles of interest from background and noise. "Trigger" refers to a preset threshold for detection of a parameter. It is typically used as a means for detecting passage of particle through the laser beam. Detection of an event which exceeds the preset threshold for the selected parameter triggers acquisition of light scatter and fluorescence data for the particle. Data is not acquired for particles or other components in the medium being assayed which cause a response below the threshold. The trigger parameter may be the detection of forward scattered light caused by passage of a particle through the light beam. The flow cytometer then detects and collects the light scatter and fluorescence data for particle.

A particular subpopulation of interest may be further analyzed by "gating" based on the data collected for the entire sample. To select an appropriate gate, the data is plotted so as to obtain the best separation of subpopulations possible. This procedure is typically done by plotting forward light scatter (FSC) vs. side (i.e., orthogonal) light scatter (SSC) on a two dimensional dot plot. The flow cytometer operator then selects the desired subpopulation of particles (i.e., those cells within the gate) and excludes particles which are not within the gate. Where desired, the operator may select the gate by drawing a line around the desired subpopulation using a cursor on a computer screen. Only those particles within the gate are then further analyzed by plotting the other parameters for these particles, such as fluorescence. Gating based on fluorescence may then be used to further separate subpopulations of cells. For example, MSCs may be gated according to the strategy outlined in FIG. 1. The gated MSCs may then be further assessed as described below.

In certain aspects, the method further includes providing an assessment of the immunomodulatory potential of the MSC population. The assessment may be based on the previously described CD54/IL-6 result. Optionally further, the assessment may be also be based on the additional result (obtained from the signal of one or more additional detectable labels specific for additional biomarkers, as described previously). The assessment may be provided as a digital, qualitative or a quantitative assessment. For example, the MSC population may be assessed as having an enhanced immunomodulatory potential when the result (e.g., CD54/IL-6 and/or additional result) is above a threshold. The threshold may be predetermined, or may be determined based on a standardized control.

In some embodiments, the MSC is determined to have an enhanced immunomodulatory potential when the median fluorescence intensity (e.g., as determined by flow cytometry) of detectable labels bound to CD54 associated with the MSC exceeds a predetermined threshold. For example, in embodiments the MSC may be determined as having enhanced immunomodulatory potential when the median fluorescence intensity of detectable labels bound to CD54 associated with the MSC exceeds 250 or greater, such as 500 or greater, such as 750 or greater and including a median fluorescence intensity of 1000 or greater. In other embodiments, the MSC is determined to have an enhanced immunomodulatory potential when the median fluorescence intensity (e.g., as determined by flow cytometry) of detectable labels bound to IL-6 associated with the MSC as exceeds a predetermined threshold, such as where the median fluorescence intensity of detectable labels bound to IL-6 associated with the MSC exceeds a threshold of 1000 or greater, such as 1500 or greater, such as 2000 or greater, such as 2500 or greater, such as 5000 or greater and including a median fluorescence intensity of 10000 or greater.

In certain embodiments, methods further include determining a median fluorescence intensity (MFI) threshold for assessing whether the MSC has enhanced immunomodulatory potential. In some instances, the median fluorescence intensity (MFI) threshold is determined by measuring the median fluorescence intensity of detectable labels bound to a biomarker associated with control cells from one or more MSC populations with high immunomodulatory potential. In certain instances, determining a median fluorescence intensity threshold includes taking the average median fluorescence intensity of detectable labels bound to the biomarker associated with the control cells from two or more different MSC populations with high immunomodulatory potential, such as three or more different MSC populations with high immunomodulatory potential, such as four or more and including five or more different MSC populations with high immunomodulatory potential. In one example, methods include determining a median fluorescence intensity threshold of detectable labels bound to CD54 associated with the MSC. In another example, methods include determining a median fluorescence intensity threshold of detectable labels bound to IL-6 associated with the MSC.

In other embodiments, the MSC is determined to have an enhanced immunomodulatory potential when the percentage of the MSC population having a fluorescence intensity of detectable labels bound to CD54 (e.g., as measured by flow cytometry) exceeding a predetermined threshold is above a particular cut-off point. For example, in some instances the MSC is determined to have an enhanced immunomodulatory potential when 2% or greater of the MSC population has a fluorescence intensity of detectable labels bound to CD54 exceeding a predetermined threshold, such as 5% or greater, such as 10% or greater, such as 25% or greater, such as 50% or greater, such as 75% or greater and including when 90% or greater of the MSC population has a fluorescence intensity of detectable labels bound to CD54 exceeding a predetermined threshold. In these instances, predetermined threshold of fluorescence intensity of detectable labels bound to CD54 may vary, such as a fluorescence intensity of 250 or greater, such as 500 or greater, such as 750 or greater, such as 1000 or greater, such as 1500 or greater and including a fluorescence intensity of 5000 or greater.

In still other embodiments, the MSC is determined to have an enhanced immunomodulatory potential when the percentage of the MSC population having a fluorescence intensity of detectable labels bound to IL-6 (e.g., as measured by flow cytometry) exceeding a predetermined threshold is above a particular cut-off point. For example, in some instances the MSC is determined to have an enhanced immunomodulatory potential when 2% or greater of the MSC population has a fluorescence intensity of detectable labels bound to IL-6 exceeding a predetermined threshold, such as 5% or greater, such as 10% or greater, such as 25% or greater, such as 50% or greater, such as 75% or greater and including when 90% or greater of the MSC population has a fluorescence intensity of detectable labels bound to IL-6 exceeding a predetermined threshold. In these instances, predetermined threshold of fluorescence intensity of detectable labels bound to IL-6 may vary, such as a fluorescence intensity of 1000 or greater, such as 1500 or greater, such as 2000 or greater, such as 2500 or greater, such as 5000 or greater and including a fluorescence intensity of 10000 or greater.

In some embodiments, the MSC is determined to have an enhanced immunomodulatory potential when compared to a standardized control. In one example, the standardized control may be control particles, such as fluorescent control beads or control cells. The control particles may serve as a positive or negative control. For example, control cells from an MSC population with high immunomodulatory potential may have a relatively high CD54/IL-6 result (i.e., a high expression of CD54 and IL-6). The control cells CD54/IL-6 result may be set as the threshold. If quantification of the detectable labels of the labeled sample obtains a higher CD54/IL-6 result than this threshold, the MSC population of the labeled sample may be assessed to have an enhanced (or high) immunomodulatory potential.

In certain embodiments, methods include determining whether an MSC population is suitable for employing as positive control. In some instances, the MSC population is determined to be suitable for employing as a positive control where the MSC suppresses or reduces expression of one or more biomarkers by activated immune cells (e.g., T-cells, B-cells, NK-cells, PBMCs or combinations thereof as described above), such as by 10% or more, such as 25% or more, such as by 50% or more, such as by 75% or more and including by 90% or more or by 2-fold or more, such as 3-fold or more, such as 5-fold or more and including by 10-fold or more. For example, the MSC population may be determined to be suitable for employing as a positive control where the MSC suppresses or reduces CD3 expression by activated T-cells by 10% or more, such as 25% or more, such as by 50% or more, such as by 75% or more and including by 90% or more. In other instances, the MSC population is determined to be suitable for employing as a positive control where the reduces CD3 expression by activated T-cells by 2-fold or more, such as 3-fold or more, such as 5-fold or more and including reducing CD3 expression by activated T-cells by 10-fold or more.

In other instances, the MSC population is determined to be suitable for employing as a positive control where the MSC suppresses or reduces IFN-γ expression by activated T-cells by 10% or more, such as 25% or more, such as by 50% or more, such as by 75% or more and including by 90% or more. In other instances, the MSC population is determined to be suitable for employing as a positive control where the MSC reduces IFN-γ expression by activated T-cells by 2-fold or more, such as 3-fold or more, such as 5-fold or more and including reducing IFN-γ expression by activated T-cells by 10-fold or more.

In some embodiments, the MSC population is determined to be suitable for employing as a positive control where the MSC exhibits a median fluorescence intensity (e.g., as determined by flow cytometry) of CD54 which exceeds a predetermined threshold, such as a median fluorescence intensity of CD54 that exceeds 250 or greater, such as 500 or greater, such as 750 or greater and including a median fluorescence intensity of 1000 or greater. In other embodiments, the MSC population is determined to be suitable for employing as a positive control where the MSC exhibits a median fluorescence intensity (e.g., as determined by flow cytometry) of IL-6 which exceeds a predetermined threshold, such as a median fluorescence intensity of CD54 that exceeds 1000 or greater, such as 1500 or greater, such as 2000 or greater, such as 2500 or greater, such as 5000 or greater and including a median fluorescence intensity of 10000 or greater.

In additional aspects, multiple samples from different MSC populations may be compared based on their CD54/IL-6 results, and optionally further based on their additional results.

As previously described, the tissue of origin and culture conditions can lead to MSC populations with different characteristics (such as surface marker expression) and immunomodulatory properties. As such, different batches of MSCs may exhibit different therapeutic efficacy. The assessment of the immunomodulatory potential of the MSC population may therefore be used as a quality control of a MSC therapeutic regimen. In certain embodiments, a MSC population may or may not be used therapeutically based on the assessment of whether the MSC population has enhanced immunomodulatory potential.

A number of potential and known therapeutic uses of MSCs are within the embodiments disclosed herein. Specifically, the MSC population may be used in the treatment or prevention of a disease characterized by autoimmunity and/or inflammation, such as graft-versus-host disease (GvHD), Chron's disease, type I diabetes mellitus, multiple sclerosis, rheumatoid arthritis, scleroderma and other autoimmune and/or inflammatory diseases familiar to one of ordinary skill in the art. A review of MSC therapeutic trials for Chron's disease is provided by Dalal J et al. 2012, Pediatr Res. 71(4 Pt 2):445-51, the disclosure of which is incorporated herein by reference. A description of a clinical trial of a MSC-based therapy for GvHD is provided by Le Blanc K et al. 2008, Lancet 10; 371(9624):1579-86, the disclosure of which is incorporated herein by reference. Therapeutic use of MSCs in treatment of other diseases not primarily characterized by autoimmunity and/or inflammation, such as myocardial infarction, chronic obstructive pulmonary disease, and certain degenerative diseases (e.g., osteogenesis imperfecta) are also within the scope of the embodiments disclosed herein. A general review of MSC therapeutics is provided by Parekkadan B. et al., Annu Rev Biomed Eng. (2010) 12: 87-117.

For the purposes of the invention, the MSC population may be allogeneic, autologous, or xenogeneic with respect to the recipient. MSCs are at least partially protected from immune rejection, and therefore a perfect match of histocompatibility antigens is not required for allogeneic transplantation. In some instances, at least one HLA match is provided, more usually two matches, three matches, four matches, five matches, or more. The number of cells to be transplanted will vary with the specific treatment that is desired, the size of the recipient, and the like. In general, for a human, a dose of MSCs may comprise $10^5$ cells, and often $10^6$ cells, $10^7$ cells, or $10^8$ cells or more. Doses of MSCs may be administered to the patient, for example, once a day, multiple times a week, once a week, or once a month. The MSCs may be administered locally (e.g., at the location of the afflicted tissue or at a location from which MSCs could traffic to the afflicted tissue) and/or systemically.

In one example, the MSCs may be administered alongside cells or a tissue of interest (e.g., to prevent rejection of a transplantation). Cells of interest for transplantation include, without limitation, cardiomyocytes and progenitors thereof; neural progenitor cells, e.g., for the regeneration of neurons, or retina, and the like; pancreatic islet cells, particularly pancreatic B-cells; hematopoietic stem and progenitor cells; muscle satellite cells; endothelial cells or progenitors thereof; and the like. Tissues of interest include liver tissue, kidney tissue, heart tissue, lung tissues, skin tissue, brain tissue; spinal cord tissue; pancreatic islets; retinal tissue; bone marrow; and the like.

For general principles in medicinal formulation, the reader is referred to Cell Therapy: Stem Cell Transplantation, Gene Therapy, and Cellular Immunotherapy, by G. Morstyn & W. Sheridan eds, Cambridge University Press, 1996. Choice of the cellular excipient and any accompanying elements of the composition will be adapted in accordance with the route and device used for administration. The cells may be introduced by injection, catheter, or the like. The cells may be frozen at liquid nitrogen temperatures and stored for long periods of time, being capable of use on thawing.

Devices and Systems

Aspects of the invention further include systems for use in practicing the subject methods. Systems of the invention may include a flow cytometer configured to assay particles (e.g., beads, cells such as MSCs, etc.) by measuring signals such as FSC, SSC, fluorescence emission maxima, light scatter, mass, molecular mass, etc. The system may further include a signal processing module configured to receive the signals and output an assessment of the immunomodulatory potential of a MSC population. Flow cytometers of interest include, but are not limited, to those devices described in U.S. Pat. Nos. 4,704,891; 4,727,029; 4,745,285; 4,867,908; 5,342,790; 5,620,842; 5,627,037; 5,701,012; 5,895,922; and 6,287,791; the disclosures of which are herein incorporated by reference. In some instances, the flow cytometer includes: a flow channel; a detector module that includes a first detector configured to receive a first signal from the assay region of the flow channel and a second detector configured to receive a second signal from the assay region of the flow channel. The flow cytometer may optionally further include at least a first light source configured to direct light to an assay region of the flow channel (where in some instances the cytometer includes two or more light sources). In certain aspects, the first signal may be produced by a detectable label that specifically binds to CD54 and the second signal may be produced by a detectable label that specifically binds to IL-6. Optionally further, the flow cytometer may include one or more additional detectors and/or light sources for the detection of one or more additional signals. The one or more additional signals may be produced by one or more additional detectable labels that specifically bind to biomarkers indicative of the immunomodulatory potential of the MSC population.

Aspects of the invention further include a signal processing module configured to receive signals from the first and second detectors and output an assessment of the immunomodulatory potential of a MSC population (e.g., whether or not the MSC population has enhanced immunomodulatory potential, as described earlier). The signal processing module may be integrated into the cytometer as a single device, or distributed from the cytometer where the signal processing module and cytometer are in communication with each other, e.g., via a wired or wireless communication protocol. Additional aspects of the signal processing module are further described in the computer related embodiments section below.

Accordingly, aspects of the invention further include systems, e.g., computer-based systems, which are configured to detect the presence of a first and second detectable signal, e.g., as described above. A "computer-based system" refers to the hardware means, software means, and data storage means used to analyze the information of the present invention. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can access such a manufacture.

To "record" data, programming or other information on a computer readable medium refers to a process for storing information, using any such methods as known in the art. Any convenient data storage structure may be chosen, based on the means used to access the stored information. A variety of data processor programs and formats can be used for storage, e.g., word processing text file, database format, etc.

A "processor" references any hardware and/or software combination that will perform the functions required of it. For example, any processor herein may be a programmable digital microprocessor such as available in the form of an electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

In addition to the sensor device and signal processing module, e.g., as described above, systems of the invention may include a number of additional components, such as data output devices, e.g., monitors and/or speakers, data input devices, e.g., interface ports, keyboards, etc., fluid handling components, power sources, etc.

In some instances, the systems may further include a sample (e.g., loaded on the flow channel), as prepared according to any of the aspects of the subject methods described above. In certain aspects, the flow cytometer may be a fluorescence activated cell sorter (FACS) instrument or a mass cytometer. In another aspect, the system may be a fluorimeter.

Utility

The subject methods and systems find use in a variety of different applications where assessment of the immunomodulatory potential of a MSC population is desired. Such applications include quality control of therapeutic regimens as well as research, and prognostic applications. For example, assessment of whether a MSC population displays a specific signature (CD54+IL6+) that is predictive of enhanced (or sufficient) immunomodulatory potential may guide whether the MSC population is useful in a cellular therapy, and thereby improving standard of care through quality control. Furthermore, two or more MSC populations can be compared based on assessed immunomodulatory potential, and the MSC population assessed to have the highest immunomodulatory potential may be used in a therapeutic regimen. In research applications, the subject methods may be used to check the effect of MSC culture conditions on MSC immunomodulatory potential. In assessing a prognosis of a patient treated with an MSC-based cell therapy, an assessment of the immunomodulatory potential of the MSC population used in the cell therapy may be used to predict outcome.

The above described applications of the subject methods and systems are convenient as they involve a single assay that is not time intensive. This can be compared to a combination of assays, such as flow cytometry and ELISA that are often used for the determination of surface and cytokine signature, respectively. Furthermore, functional assays of MSC immunomodulatory activity that often require co-culture of MSCs with PBMCs, T-cells, B-cells, NK cells, monocytes, etc. In comparison, the subject methods and systems provide for an assay that is less time intensive and does not require cell types other than MSCs.

Embodiments of the methods and compositions described herein also find use in the purification of MSC subsets with high immunomodulatory capacity based on the expression of the surface marker CD54. Cell purification can be achieved via FACS sorting or magnetic selection, e.g., as described above. Such may or may not be done in conjunction with IL6 detection and/or sorting.

Computer Related Embodiments

Aspects of the invention further include a variety of computer-related embodiments. Specifically, the quantitation and assessment steps of the methods described in the previous sections may be performed using a computer. Accordingly, the invention provides a computer-based system for analyzing data produced using the above methods in order to quantitate an amount of a first, second, and/or additional detectable labels and to provide an assessment of whether an MSC population has enhance immunomodulatory potential.

In certain embodiments, the methods are coded onto a physical computer-readable medium in the form of "programming", where the term "computer readable medium" as used herein refers to any storage or transmission medium that participates in providing instructions and/or data to a computer for execution and/or processing. Examples of storage media include floppy disks, magnetic tape, CD-ROM, a hard disk drive, a ROM or integrated circuit, a magneto-optical disk, or a computer readable card such as a PCMCIA card and the like, whether or not such devices are internal or external to the computer. A file containing information (e.g., light scatter and/or fluorescence signals associated with one or more "events", a CD54/IL-6 result, a threshold above which a CD54/IL-6 result may be indicative of a MSC population with enhanced immunomodulatory potential, etc.) may be "stored" on computer readable medium, where "storing" means recording information such that it is accessible and retrievable at a later date by a computer. In certain aspects, the information may be stored in a "permanent memory" (i.e. memory that is not erased by termination of the electrical supply to a computer or processor) or "non-permanent memory". Computer hard-drive, CD-ROM, floppy disk and DVD are all examples of permanent memory. Random Access Memory (RAM) is an example of non-permanent memory. A file in permanent memory may be editable and re-writable.

In certain aspects, a module (such as the signal processing module of the previously described system) may be for the identification of mesenchymal stromal cells (MSCs) with enhanced immunomodulatory potential. The module may be configured to receive a first and second signal (such as a fluorescence emission maxima and/or intensity, fluorescence lifetime, light scatter, mass, molecular mass, etc.) from a detector. The detector may, for example, be part of a flow cytometric system, a fluorimeter, or any convenient system for implementing the subject methods. The first signal may be produced by a first detectable label that specifically binds to CD54 and the second signal may be produced by a second detectable label that specifically binds to IL-6. Optionally further, the module may be configured to receive one or more additional signals produced by additional detectable labels that bind to biomarkers indicative of MSC immunomodulatory potential.

The module may also be configured to process the first and second signals to obtain a CD54/IL-6 result. Optionally further, the module may be configured to process the one or more additional signals to obtain an additional result. The module may be configured to output an assessment of the immunomodulatory potential of the MSC population based on the CD54/IL-6 and/or additional result. The module may output the assessment based on whether the CD54/IL-6 and/or additional result are above a threshold. The module may be configured to determine the threshold based on comparison to another MSC population and/or a standardized control (e.g., as described in the subject methods). Further, the module may be configured to automatically gate MSCs from other cells based on FSC, SSC, and/or fluorescence, prior to obtaining the CD54/IL-6 result. For example, the module may be configured to gate the MSCs based on the gating strategy of FIG. 1, based on the MSC surface markers described earlier, etc.

In certain aspects, the module may be part of fluorescence activated cell sorter (FACS) system or a mass cytometric system.

Kits

In yet another aspect, the present invention provides kits for practicing the subject methods, e.g., as described above. The subject kits may include a first and second detectable label and optionally one or more additional detectable labels. The first detectable label may specifically bind to CD54 and a second detectable label may specifically bind to IL-6. The detectable labels (e.g., first, second, and/or additional detectable labels) may be as described in any of the aspects of the subject methods. In addition, the kit may include one or more protein transport inhibitors (e.g., Brefeldin A, Monensin, etc.). The kit may also include one or more cell fixing reagents such as paraformaldehyde, glutaraldehyde, methanol, acetone, formalin, or any combinations or buffers thereof. Further, the kit may include a cell permeabilizing reagent, such as methanol, acetone or a detergent (e.g., triton, NP-40, saponin, tween 20, digitonin, leucoperm, or any combinations or buffers thereof. Other protein transport inhibitors, cell fixing reagents and cell permeabilizing reagents familiar to the skilled artisan are within the scope of the subject kits.

The kit may further include reagents for performing a flow cytometric assay. Examples of said reagents include buffers for at least one of reconstitution and dilution of the first and second detectable molecules, buffers for contacting a cell sample with one or both of the first and second detectable molecules, wash buffers, control cells, control beads, fluorescent beads for flow cytometer calibration and combinations thereof.

The detectable labels and/or reagents described above may be provided in liquid or dry (e.g., lyophilized) form. Any of the above components (detectable labels and/or reagents) may be present in separate containers (e.g., separate tubes, bottles, or wells in a multi-well strip or plate). In addition, one or more components may be combined into a single container, e.g., a glass or plastic vial, tube or bottle.

In certain aspects, the kit may include one or more standardized controls. The standardized controls may be control particles such as control beads or control cells. For example, negative control cells may be from an MSC population with low immunomodulatory potential and/or low expression of CD54/IL-6. Positive control cells may be from an MSC population with enhanced immunomodulatory potential and/or high expression of CD54/IL-6.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, DVD, portable flash drive, etc., on which the information has been recorded. Yet another means that may be present is a website address which may be used via the internet to access the information at a removed site. Any convenient means may be present in the kits.

The following examples are offered by way of illustration and not by way of limitation.

EXPERIMENTAL

Example 1

Methods

Stimulated peripheral blood mononuclear cells (PBMCs) were cultured alone, co-cultured with bone marrow derived MSCs (BM MSCs), and co-cultured with adipose tissue derived MSCs (AT MSCs). T-cells (CD3+ PBMCs) were gated according to the strategy outlined in FIG. 1. T-cell expression of IFN-γ and levels of violet proliferation dye (VPD) were assayed by flow cytometry. Resting PBMCs were provided as a negative control.

Results (FIG. 2)

T-cell activation, as measured by IFN-γ expression and by T-cell proliferation, is suppressed in co-culture of stimulated PBMCs with either BM MSCs or AT MSCs. AT MSCs suppress T-cell IFN-γ expression more strongly than BM MSCs. AT MSCs completely abolish T cell proliferation, whereas BM MSC inhibition seems to be delayed by one generation.

Example 2

Methods

BM MSCs and AT MSCs were cultured alone or in co-culture with stimulated PBMCs. BM MSCs were gated according to the strategy outlined in FIG. 1. MSC expression of CD54, CD274, and IL-6 was assayed by flow cytometry.

Figure 3:
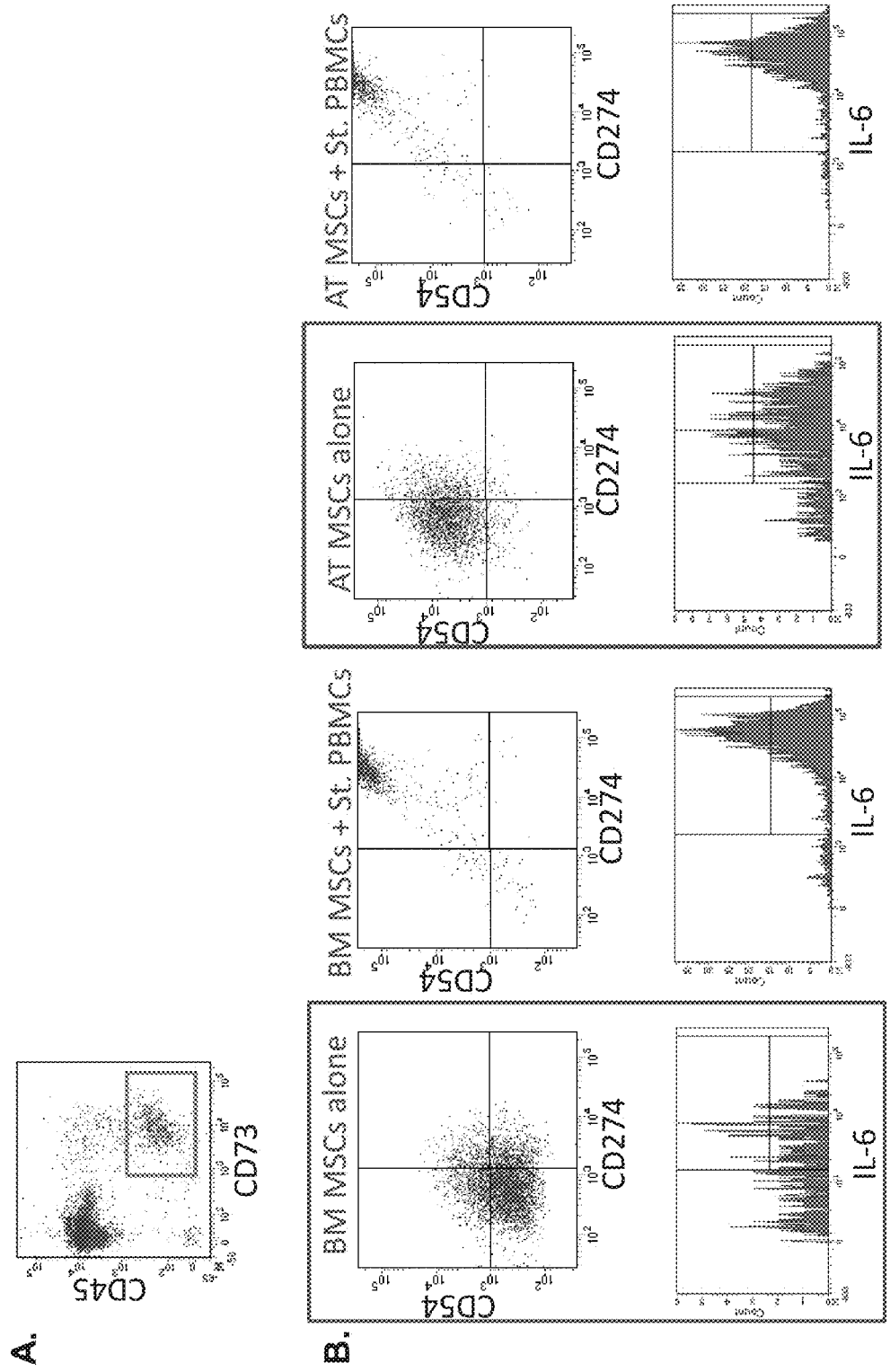
FIG. 3 panels A and B provide results of a flow cytometric assay showing the expression of CD54, CD274 and IL-6 in BM MSCs or AT MSCs.

Results (FIG. 3)

Resting AT MSCs express higher levels of CD54 and IL-6 as compared to resting BM MSCs. Upon activation through co-culture with stimulated PBMCs, both BM MSC and AT MSC populations express higher levels of CD54, CD274, and IL-6 as compared to their negative controls.

Example 3

Methods

Resting BM MSC and resting AT MSC expression of CD54 and IL-6 was assayed by flow cytometry. T-cell IFN-γ expression and VPD levels after co-culture with BM MSCs or AT MSCs was assayed by flow cytometry.

Figure 4:
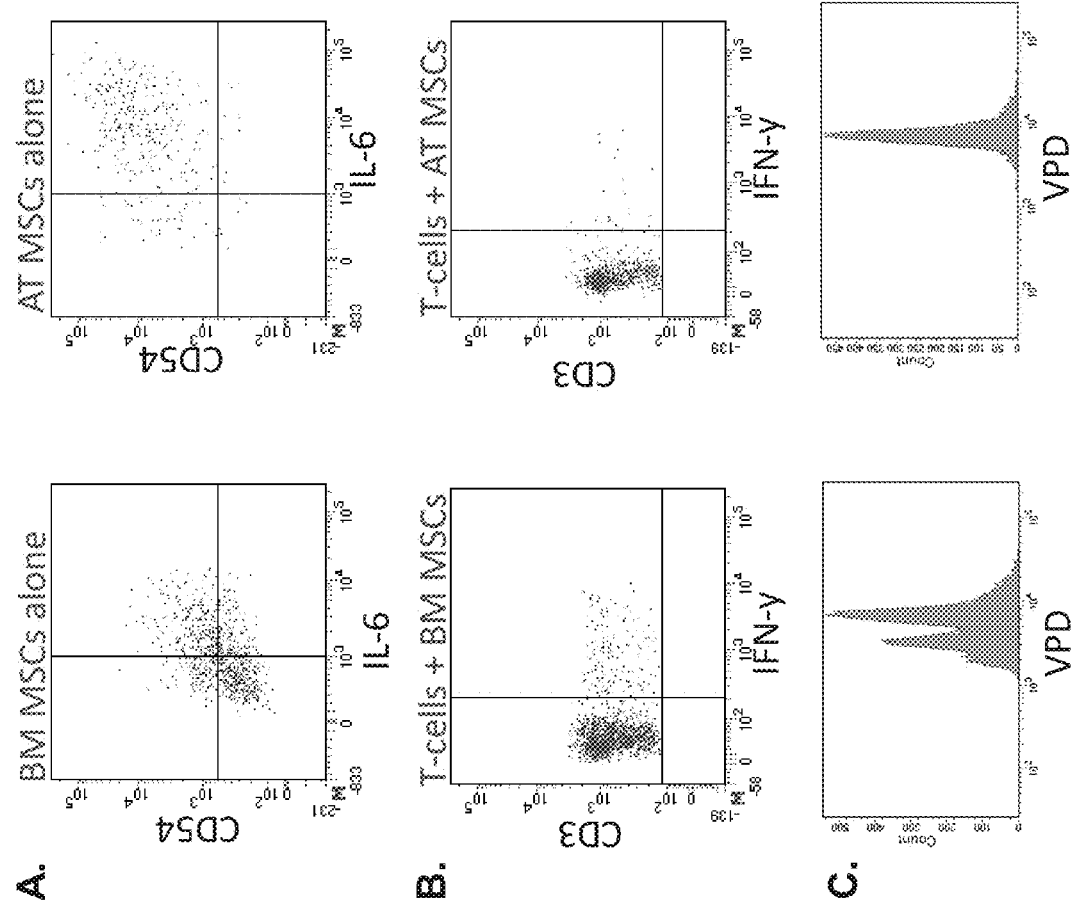
FIG. 4 panels A to C provide results of a flow cytometric assay showing expression of CD54 and IL-6 in resting BM MSCs and AT MSCs.

Results (FIG. 4)

Higher expression of CD54 and IL-6 in the AT MSC population correlates with enhanced immunomodulation as measured by inhibition of IFN-γ expression and proliferation in T-cells.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of determining immunomodulatory potential of a multipotent stromal cell population, the method comprising:
   (a) producing a multipotent stromal cell (MSC) population comprising MSCs;
   (b) contacting a sample of the MSC population with:
      (i) a CD54 detectible label comprising a first label domain and a CD54 specific binding domain; and
      (ii) an IL-6 detectible label comprising a second label domain and an IL-6 specific binding domain,
   under conditions sufficient for the CD54 detectible label to bind to CD54 present on the MSCs and for the IL-6 detectible label to bind to IL-6 inside of the MSCs to produce a labeled sample comprising detectibly labeled MSCs; and (c) quantitating the amount of CD54 on the surface of a detectibly-labeled MSC and the amount of IL-6 inside of the detectibly-labeled MSC of the labeled sample to obtain a CD54/IL-6 result for the labeled sample wherein the CD54/IL-6 result provides a determination of the immunomodulatory potential of the MSC population.

2. The method according to claim 1, wherein the MSC population is produced by:
   obtaining stem cells from human tissue; and
   culturing the stem cells under culture conditions suitable for MSC production.

3. The method according to claim 2, wherein the human tissue is bone marrow.

4. The method according to claim 2, wherein the human tissue is adipose tissue.

5. The method according to claim 1, further comprising treating the sample with a protein transport inhibitor.

6. The method according to claim 1, further comprising treating the sample with a fixation reagent prior to contacting the sample with the IL-6 detectable label.

7. The method according to claim 1, further comprising treating the sample with a permeabilization reagent prior to contacting the sample with the IL-6 detectable label.

8. The method according to claim 1, further comprising contacting the sample with an additional detectable label that specifically binds to another MSC biomarker that is different from CD54 and IL-6.

9. The method according to claim 1, wherein the specific binding domain of each of the CD54 and IL-6 detectable labels comprises an antibody or an antigen binding fragment thereof.

10. The method according to claim 1, wherein the label domain of each of the CD54 and IL-6 detectable labels comprises a fluorescent label.

11. The method according to claim 1, wherein the quantitating of step c) comprises flow cytometry.

12. The method according to claim 1, further comprising comparing the CD54/IL-6 result to a fluorescence intensity of a predetermined threshold.

13. The method according to claim 12, further comprising:
   determining the fluorescence intensity of the predetermined threshold.

14. The method according to claim 12, further comprising administering the MSC population to a subject in a therapeutic regimen if the CD54/IL-6 result is above the predetermined threshold.

15. The method according to claim 14, wherein the therapeutic regimen treats a disease selected from the group consisting of GvHd, Crohn's disease, type 1 diabetes mellitus, multiple sclerosis, rheumatoid arthritis and scleroderma.

16. The method according to claim 12, further comprising administering the MSC population to a subject to prevent rejection of a transplantation if the CD54/IL-6 result is above the predetermined threshold.

17. The method according to claim 1, wherein the method further comprises enriching MSCs from the MSC population following obtainment of the CD54/IL-6 result.

18. A cell composition comprising:
   an aliquot of a multipotent stromal cell (MSC) population;
   a CD54 detectable label comprising a first label domain and a CD54 specific binding domain wherein the CD54 detectable label binds to CD54 present on an MSC of the cell composition; and
   an IL-6 detectable label comprising a second label domain and an IL-6 specific binding domain, wherein the IL-6 detectable label binds to IL-6 inside of an MSC of the cell composition.

* * * * *